United States Patent [19]

Tokizawa et al.

[11] Patent Number: 4,849,512
[45] Date of Patent: Jul. 18, 1989

[54] 3-ACYLAMINO-3-DEOXYALLOSE DERIVATIVES

[75] Inventors: Minoru Tokizawa, Narita; Mari Otsuka, Narashino; Kazuhiko Irinoda, Chiba; Seiji Ishizeki, Tone; Fumio Ishii, Ageo; Kenichi Kukita, Kashiwa; Hideaki Matsuda, Abiko; Tatsuhiko Katori, Tone, all of Japan

[73] Assignee: SS Pharmaceutical Co., Ltd., Tokyo, Japan

[21] Appl. No.: 177,483

[22] Filed: Apr. 1, 1988

[30] Foreign Application Priority Data

Apr. 3, 1987 [JP] Japan .................... 62-82580

[51] Int. Cl.$^4$ .................... C07G 3/00; C08B 37/00
[52] U.S. Cl. .................... 536/4.1; 536/53
[58] Field of Search ............ 536/4.1, 53, 18.7, 17.2, 536/17.7, 115, 120, 117

[56] References Cited

U.S. PATENT DOCUMENTS 4,251,520 2/1988 Bruzzesse .................... 536/4.1

FOREIGN PATENT DOCUMENTS 282392 6/1986 Japan .

OTHER PUBLICATIONS

Chemical Abstracts, vol. 93, No. 7, Aug. 18, 1980; Abstract No. 93:72230(t).
Chemical Abstracts, vol. 85, No. 11; Sep. 13, 1976; Abstract No. 85:78290(u).
Chemical Abstracts, vol. 83, No. 21; Nov. 21, 1975; Abstract No. 83:179459(v).
Chemical Abstracts, vol. 84, No. 19; May 10, 1976; Abstract No. 84:136020(y).

Primary Examiner—Johnnie R. Brown
Assistant Examiner—Pamela S. Webber
Attorney, Agent, or Firm—Oblon, Spivak, McClelland, Maier & Neustadt

[57] ABSTRACT

Derivatives of 3-acylamino-3-deoxyallose represented by the following formula:

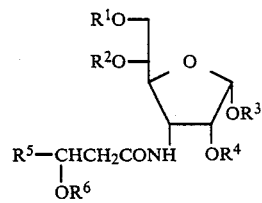

wherein $R^1$, $R^2$, $R^3$ and $R^4$ may be hydrogen atoms, or $R^1$ and $R^2$, and $R^3$ and $R^4$ may be in combination an isopropylidene group, $R^5$ represents a hydrogen atom or alkyl group, and $R^6$ represents a hydrogen atom or acyl group, are disclosed. One of the typical compound 3-deoxy-3-(3-tetradecanoyloxytetradecanoylamino)-1,2:5,6-di-O-isopropylidene- α-D-allofuranose is prepared by reacting 3-tetradecanoyloxytetradecanoic acid and 3-amino-3-deoxy-1,2:5,6-di-O-isopropylidene-α-D-allofuranose in the presence of N,N'-dicyclohexylcarbodiimide, as a dehydrating agent. The compound has an excellent carcinostatic activity.

1 Claim, No Drawings

3-ACYLAMINO-3-DEOXYALLOSE DERIVATIVES

BACKGROUND OF THE INVENTION

1. Field of the Invention:

This invention relates to novel 3-acylamino-3-deoxyallose derivatives, and, more particularly, to 3-acylamino-3-deoxyallose derivatives which are useful as a medicine.

DESCRIPTION OF THE BACKGROUND

Allose is a sugar which occurs very sparingly in nature. The only known usage of allose is as an intermediate for synthesizing other sugars. Also, only 3-acetylamino derivatives and 3-trifluoroacetylamino derivatives are known in the art as derivatives of 3-acylamino-3-deoxyallose derivatives. These are the derivatives of allose, the third positions of which are substituted with an acylamino group. However, no knowledge has yet surfaced concerining the medicinal effect of these derivatives.

The present inventors have synthesized various derivatives of 3-acylamino-3-deoxyallose and conducted extensive research into their physiological activities. As a result the inventors found that 3-acylamino-3-deoxyallose derivatives represented by the following general formula (I) exhibit excellent carcinostatic activity:

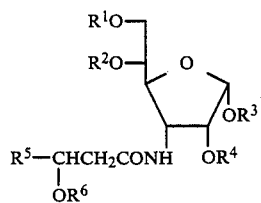

wherein $R^1$ and $R^2$ are hydrogen atoms or represent in combination an isopropylidene group, $R^3$ and $R^4$ are hydrogen, atoms or represent in combination an isopropylidene group, $R^5$ represents a hydrogen atom or alkyl group, and $R^6$ represents a hydrogen atom or acyl group. This finding has led to the completion of the invention.

SUMMARY OF THE INVENTION

Accordingly, an object of this invention is to provide 3-acylamino-3-deoxyallose derivatives represented by the above general formula (I).

Other objects, features, and advantages of this invention will appear more fully from the following description.

DETAILED DESCRIPTION OF THE INVENTION AND PREFERRED EMBODIMENTS

Compound (I) of this invention can be prepared, for example, by any of the following processes.

Process I

3-Amino-3-deoxy-1,2:5,6-di-O-isopropylidene-α-D-allofuranose (II) is reacted with a carboxylic acid (III) or its active derivative to produce as a condensation product 3-acylamino-3-deoxy-1,2:5,6-di-O-isopropylidene-α-D-allofuranose (Ia) according to the following reaction formula:

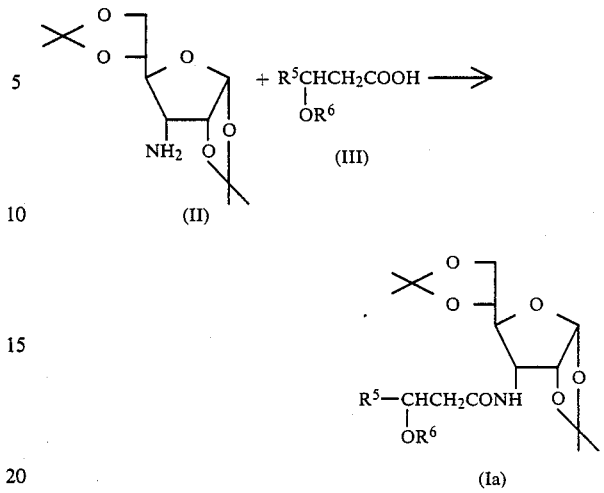

in which $R^5$ and $R^6$ have the same meanings as defined above.

The target compound (Ia) may be produced by reacting 1-1.2 mols of compound (II) with 1 mol of compound (III) in the presence of a solvent and dehydrating agent, at any temperature in the range from room temperature to the refluxing temperature of the solvent for 1-10 hours. A desirable example of the dehydrating agent is N,N'-dicyclohexylcarbodiimide, and a hydrocarbon, ether, or the like is used as a solvent. Especially preferable solvents are aromatic hydrocarbons. Upon completion of the reaction, compound (Ia) is collected by distilling off the solvent and subjecting the residue to silica gel column chromatography or the like purification means.

Process II

3-Acylamino-3-deoxy-1,2:5,6-di-O-isopropylidene-α-D-allofuranose (Ia) is hydrolyzed with an acid at a temperature ranging from 0° C. to room temperature to give 3-acylamino-3-deoxy-1,2-O-isopropylidene-α-D-allofuranose (Ib) according to the following reaction formula:

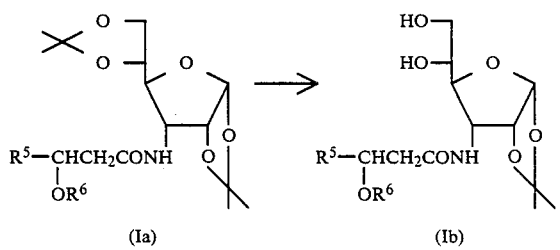

in which $R^5$ and $R^6$ have the same meanings as defined above.

The reaction may be carried out by dissolving compound (Ia) in a solvent such as methanol or the like, and in the presence of a small amount of an acid at a temperature of 0° C.—room temperature for a period of 1-10 hours. Desirable as an acid is a mineral acid, hydrochloric acid in particular. Upon completion of the reaction, the reaction mixture is neutralized with sodium bicarbonate or the like and then condensed, followed by purification by silica gel column chromatography or the like to obtain compound (Ib).

Process III

3-Acylamino-3-deoxy-1,2:5,6-di-O-isopropylidene-α-D-allofuranose (Ia) is hydrolyzed with an acid at a temperature ranging from room temperature to 80° C. to give 3-acylamino-3-deoxy-D-allofuranose (Ic) according to the following reaction formula:

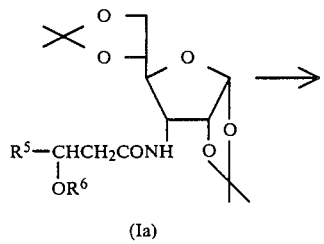

(Ia)

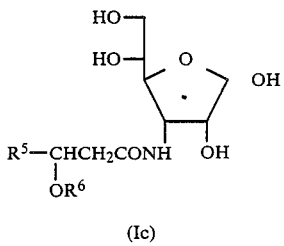

(Ic)

in which $R^5$ and $R^6$ have the same meanings as defined above.

This reaction may be carried out by treating compound (Ia) with a mineral acid such as hydrochloric acid at a temperature ranging from room temperature to 80° C. for 2–10 hours. The target compound deposits as crystals by ice-cooling the reaction mixture.

Compound (Ic) obtained by the hydrolysis of compound (Ia) is of the allofuranose type. This compound is, however, in equilibrium with an allopyranose-type compound of the following formula (Ic'), and is usually represented by this allopyranose type (Ic'):

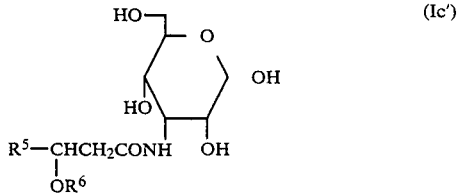

in which $R^5$ and $R^6$ has the same meanings as defined above.

Effect of the Invention

The carcinostatic effects of the compound of this invention prepared as described above have been tested, the results of which are hereafter discussed.

Groups of ICR mice, consisting of 8 mice each, were provided for the test. Ehrlich's tumor cells in the amount of $1 \times 10^5$ were inoculated intraperitoneally into each mouse. The test compound of a prescribed concentration, suspended in physiological saline water containing 2% dimethylsulfoxide—0.02% Tween 80, was intraperitoneally administered once each day, starting from the day following the inoculation and for 10 days thereafter. The carcinostatic effects (%) following the 45th day of innoculation were calculated from the average survival days of the mice by applying the following formula:

$$\text{Carcinostatic Effect (\%)} = \frac{T}{C} \times 100$$

wherein T represents the average survival days of the treated groups and C represents those of the control group.

The results are shown in Table 1.

TABLE 1

| Compound No. | Dose (mg/kg/day) | Carcinostatic Effect (%) |
|---|---|---|
| 25 | 2.5 | 170 |
|  | 10 | 132 |
|  | 40 | 193 |
|  | 160 | 225 |
| Control | — | 100 |

As evident from the above results, the compound according to this invention has an excellent carcinostatic effect.

Other features of the invention will become apparent in the course of the following description of the exemplary embodiments which are given for illustration of the invention and are not intended to be limiting thereof.

EXAMPLES

Example 1

3-Tetradecanoyloxytetradecanoic acid, 10.0 gm, was dissolved in benzene. To the solution was added 4.99 gm of N,N'-dicyclohexylcarbodiimide, and the mixture was warmed at 50° C. for 30 minutes. Then, 6.28 gm of 3-amino-3-deoxy-1,2:5,6-di-O-isopropylidene-α-D-allofuranose (II) was added, followed by refluxing for 5 hours. The resulting reaction mixture was ice-cooled to separate the deposited crystals by filtration. The filtrate thus obtained was condensed, and the residue was purified by column chromatography using toluene as an eluent to give 12.1 gm of 3-deoxy-3-(3-tetradecanoyloxytetradecanoylamino)-1,2:5,6-di-O-isopropylidene-α-D-allofuranose (Compound No. 9) at a yield of 79.0%.

Example 2

3-Deoxy-3-(3-tetradecanoyloxytetradecanoylamino)-1,2:5,6-di-O-isopropylidene-α-D-allofuranose (Compound No. 9), 12.1 gm, was dissolved in 200 ml of methanol, to which 5 ml of hydrochloric acid diluted with methanol to 10 fold by volume was added dropwise while stirring. The stirring was continued for 6 hours. Subsequently, the mixture was neutralized with saturated sodium bicarbonate solution, and condensed. The residue was then purified by column chromatography using toluene as an eluent to given 6.8 gm of 3-deoxy-3-(3-tetradecanoyloxytetradecanoylamino)-1,2-O-isopropylidene-α-D-allofuranose (Compound No. 25) at a yield of 59.6%.

Example 3

To 0.5 gm of 3-deoxy-3-(3-tetradecanoyloxytetradecanoylamino)-1,2:5,6-di-O-isopropylidene-α-D-allofuranose (Compound No. 9) was added 6 ml of 5% of hydrochloric acid, and the mixture was stirred at 50° C. for 4 hours. The resulting reaction mixture was ice-cooled to separate the deposited crystals by filtration. The crystals thus obtained were washed with a small amount of water to give 0.42 gm of 3-deoxy-3-(3-tetradecanoyloxytetradecanoylamino)-D-allofuranose (Compound No. 33) at a yield of 95.4%.

Example 4

Compounds listed in Table 2 were synthesized in a similar manner as those described in Examples 1–3. Listed also in Table 2 are compounds prepared in Examples 1–3.

TABLE 2

| Compound No. | $R^5$ | $R^6$ | Property (m.p.) | IR $\nu cm^{-1}$ | NMR(CDCL$_3$) $\delta$(ppm) |
|---|---|---|---|---|---|

Structure (Ia): $R^5$—CHCH$_2$CONH— with O$R^6$, attached to D-allofuranose with isopropylidene group.

| 1 | C$_9$H$_{19}$ | C$_{11}$H$_{23}$CO | Oily | 3320, 2940 1730, 1660 | 0.7–1.0(6H, t-like), 1.0–1.8(46H, m), 2.28(2H, t, J=6H$_z$), 2.46(2H, d, J=6H$_z$), 3.7–4.4(5H, m), 4.4–4.7(1H, t-like), 4.8–5.4(1H, m), 5.77(1H, d, J=4H$_z$), 5.9–6.2(1H, d-like) |
| 2 | C$_9$H$_{19}$ | C$_{13}$H$_{27}$CO | Oily | 3320, 2930 1730, 1650 | 0.7–1.0(6H, t-like), 1.0–1.8(50H, m), 2.28(2H, t, J=6H$_z$), 2.46(2H, d, J=6H$_z$), 3.7–4.3(5H, m), 4.4–4.7(1H, t-like), 4.8–5.4(1H, m), 5.84(1H, d, J=4H$_z$), 5.9–6.2(1H, d-like) |
| 3 | C$_9$H$_{19}$ | C$_{15}$H$_{31}$CO | Oily | 3320, 2940 1735, 1660 | 0.7–1.0(6H, t-like), 1.0–1.8(54H, m), 2.31(2H, t, J=6H$_z$), 2.50(2H, d, J=6H$_z$), 3.7–4.3(5H, m), 4.4–4.7(1H, t-like), 4.8–5.4(1H, m), 5.84(1H, d, J=4H$_z$), 5.9–6.2(1H, d-like) |
| 4 | C$_9$H$_{19}$ | C$_{17}$H$_{35}$CO | Oily | 3320, 2940 1730.1650 | 0.7–1.0(6H, t-like), 1.0–2.0(58H, m), 2.32(2H, t, J=6H$_z$), 2.48(2H, d, J=6H$_z$), 3.8–4.4(5H, m), 4.4–4.7(1H, t-like), 4.8–5.3(1H, m), 5.79(1H, d, J=4H$_z$), 5.9–6.2(1H, d-like) |
| 5 | C$_{11}$H$_{23}$ | CH$_3$CO | Oily | 3320, 2930 1740, 1660 | 0.6–1.0(3H, t-like), 1.0–1.9(32H, m), 2.03(3H, s), 2.47(2H, d, J=6H$_z$), 3.7–4.4(5H, m), 4.4–4.6(1H, t-like), 4.9–5.3(1H, m), 5.78(1H, d, J=4H$_z$), 5.9–6.2(1H, d-like) |
| 6 | C$_{11}$H$_{23}$ | C$_5$H$_{11}$CO | Oily | 3340, 2930 1730, 1645 | 0.6–1.1(6H, t-like), 1.1–1.9(38H, m), 2.28(2H, t, J=6H$_z$), 2.46(2H, d, J=6H$_z$), 3.8–4.4(5H, m), 4.4–4.7(1H, m), 4.9–5.3(1H, m), 5.76(1H, d, J=4H$_z$), 5.9–6.2(1H, d-like) |
| 7 | C$_{11}$H$_{23}$ | C$_9$H$_{19}$CO | Oily | 3340, 2930 1730, 1645 | 0.6–1.0(6H, t-like), 1.0–1.9(46H, m), 2.24(2H, t, J=6H$_z$), 2.46(2H, d, J=6H$_z$), 3.7–4.3(5H, m), 4.4–4.7(1H, t-like), 4.9–5.3(1H, m), 5.75(1H, d, J=4H$_z$), 5.9–6.1(1H, d-like) |
| 8 | C$_{11}$H$_{23}$ | C$_{11}$H$_{23}$CO | Oily | 3310, 2940 1735, 1650 | 0.6–1.0(6H, t-like), 1.0–1.8(50H, m), 2.22(2H, t, J=6H$_z$), 2.49(2H, d, J=6H$_z$), 3.7–4.3(5H, m), 4.4–4.6(1H, t-like), 4.9–5.2(1H, m), 5.74(1H, d, J=4H$_z$), 5.9–6.1(1H, d-like) |
| 9 | C$_{11}$H$_{23}$ | C$_{13}$H$_{27}$CO | Oily | 3320, 2940 1730, 1665 | 0.7–1.1(6H, t-like), 1.1–1.8(54H, m), 2.32(2H, t, J=6H$_z$), 2.49(2H, d, J=6H$_z$), 3.8–4.4(5H, m), 4.4–4.6(1H, t-like), 4.9–5.2(1H, m), 5.74(1H, d, J=4H$_z$), 5.9–6.1(1H, d-like) |
| 10 | C$_{11}$H$_{23}$ | C$_{15}$H$_{31}$CO | Oily | 3320, 2930 1735, 1650 | 0.7–1.1(6H, t-like), 1.1–1.9(58H, m), 2.26(2H, t, J=6H$_z$), 2.47(2H, d, J=6H$_z$), 3.7–4.3(5H, m), 4.4–4.7(1H, t-like), 4.9–5.3(1H, m), 5.78(1H, d, J=4H$_z$), 5.9–6.2(1H, d-like) |
| 11 | C$_{11}$H$_{23}$ | C$_{17}$H$_{35}$CO | Oily | 3300, 2940 1735, 1645 | 0.7–1.0(6H, t-like), 1.0–1.8(62H, m), 2.28(2H, t, J=6H$_z$), 2.48(2H, d, J=6H$_z$), 3.7–4.4(5H, m), 4.4–4.7(1H, t-like), 4.9–5.3(1H, m), 5.80(1H, d, J=4H$_z$), 5.9–6.2(1H, d-like) |
| 12 | C$_{13}$H$_{27}$ | C$_9$H$_{19}$CO | Oily | 3310, 2940 1735, 1645 | 0.7–1.0(6H, t-like), 1.0–1.8(50H, m), 2.30(2H, t, J=6H$_z$), 2.46(2H, d, J=6H$_z$), 3.8–4.3(5H, m), 4.4–4.7(1H, t-like), 4.9–5.4(1H, m), 5.76(1H, d, J=4H$_z$), 5.9–6.2(1H, d-like) |
| 13 | C$_{13}$H$_{27}$ | C$_{11}$H$_{23}$CO | Oily | 3310, 2940 1730, 1645 | 0.7–1.0(6H, t-like), 1.0–1.8(54H, m), 2.30(2H, t, J=6H$_z$), 2.46(2H, d, J=6H$_z$), 3.8–4.3(5H, m), 4.4–4.7(1H, t-like), 4.9–5.3(1H, m), 5.76(1H, d, J=4H$_z$), 5.9–6.2(1H, d-like) |
| 14 | C$_{13}$H$_{27}$ | C$_{13}$C$_{27}$CO | Oily | 3310, 2940 1730, 1645 | 0.7–1.0(6H, t-like), 1.0–1.8(58H, m), 2.30(2H, t, J=6H$_z$), 2.48(2H, d, J=6H$_z$), 3.7–4.3(5H, m), 4.4–4.7(1H, t-like), 4.9–5.4(1H, m), 5.79(1H, d, J=4H$_z$), 5.9–6.2(1H, d-like) |
| 15 | C$_{13}$H$_{27}$ | C$_{15}$C$_{31}$CO | Oily | 3300, 2940 1730, 1645 | 0.7–1.0(6H, t-like), 1.0–1.8(62H, m), 2.29(2H, t, J=6H$_z$), 2.47(2H, d, J=6H$_z$), 3.7–4.3(5H, m), 4.4–4.7(1H, t-like), 4.9–5.4(1H, m), 5.79(1H, d, J=4H$_z$), 5.9–6.2(1H, d-like) |

Structure (Ib): HO— and HO— on furanose ring, $R^5$—CHCH$_2$CONH— with O$R^6$.

| 16 | C$_2$H$_{19}$ | C$_{11}$H$_{23}$CO | Oily | 3350, 2940 1730, 1640 | 0.7–1.0(6H, t-like), 1.0–1.9(40H, m), 2.30(2H, t, J=6H$_z$), 2.50(2H, d, J=6H$_z$), 3.0–3.2(2H, m), 3.6–4.4(5H, m), 4.55(1H, t, J=5H$_z$), 5.77(1H, d, J=4H$_z$), 6.3–6.6(1H, d-like) |

TABLE 2-continued

| Compound No. | $R^5$ | $R^6$ | Property (m.p.) | IR $\nu cm^{-1}$ | NMR(CDCL$_3$) δ(ppm) |
|---|---|---|---|---|---|
| 17 | $C_9H_{19}$ | $C_{13}H_{27}CO$ | Oily | 3340, 2930 1730, 1640 | 0.7–1.0(6H, t-like), 1.0–1.8(44H, m), 2.30(2H, t, J=6H$_z$), 2.52(2H, d, J=6H$_z$), 2.9–3.2(2H, m), 3.5–4.3(5H, m), 4.58(1H, t, J=4H$_z$), 4.9–5.3(1H, m), 5.82(1H, d, J=4H$_z$), 6.3–6.6(1H, d-like) |
| 18 | $C_9H_{19}$ | $C_{15}H_{31}CO$ | Oily | 3340, 2940 1730, 1640 | 0.7–1.0(6H, t-like), 1.0–1.8(48H, m), 2.25(2H, t, J=6H$_z$), 2.48(2H, d, J=6H$_z$), 2.8–3.0(2H, m), 3.5–4.2(5H, m), 4.53(1H, t, J=4H$_z$), 4.8–5.2(1H, m), 5.77(1H, d, J=4H$_z$), 6.2–6.5(1H, d-like) |
| 19 | $C_9H_{19}$ | $C_{17}H_{35}CO$ | Oily | 3340, 2940 1730, 1640 | 0.7–1.0(6H, t-like), 1.0–1.9(52H, m), 2.28(2H, t, J=6H$_z$), 2.49(2H, d, J=6H$_z$), 2.8–3.1(2H, m), 3.6–4.3(5H, m), 4.53(1H, t, J=4H$_z$), 4.9–5.3(1H, m), 5.76(1H, d, J=4H$_z$), 6.3–6.6(1H, d-like) |
| 20 | $C_{11}H_{23}$ | H | Transparent crystal (92-23° C.) | 3340, 2910 1640, | 0.6–1.0(3H, t-like), 1.0–1.6(26H, m), 2.38(2H, t, J=6H$_z$), 2.8–3.1(1H, m), 3.2–4.3(7H, m), 4.60(1H, m, J=4H$_z$), 5.79(1H, d, J=4H$_z$), 6.6–6.9(1H, d-like) |
| 21 | $C_{11}H_{23}$ | $CH_3CO$ | Oily | 3350, 2930 1740, 1645 | 0.7–1.1(3H, t-like), 1.1–1.8(26H, m), 2.04(3H, s), 2.49(2H, d, J=6H$_z$), 2.9–3.2(1H, m), 3.5–4.3(6H, m), 4.58(1H, t, 4H$_z$), 4.9–5.4(1H, m), 5.76(1H, d, J=4H$_z$), 6.4–6.6(1H, d-like) |
| 22 | $C_{11}H_{23}$ | $C_5H_{11}CO$ | Oily | 3350, 2950 1735, 1650 | 0.6–1.0(6H, t-like), 1.0–1.9(32H, m), 2.30(2H, d, J=6H$_z$), 2.50(2H, d, J=6H$_z$), 3.4–4.3(7H, m), 4.57(1H, t, J=4H$_z$), 5.0–5.3(1H, m), 5.80(1H, d, J=4H$_z$), 6.3–6.6(1H, d-like) |
| 23 | $C_{11}H_{23}$ | $C_9H_{19}CO$ | Oily | 3350, 2950 1735, 1650 | 0.7–1.1(6H, t-like), 1.1–1.8(40H, m), 2.30(2H, t, J=6H$_z$), 2.52(2H, d, J=6H$_z$), 3.5–4.1(7H, m), 4.57(1H, t, J=4H$_z$), 5.0–5.3(1H, m), 5.80(1H, d, J=4H$_z$), 6.3–6.6(1H, d-like) |
| 24 | $C_{11}H_{23}$ | $C_{11}H_{23}CO$ | Oily | 3350, 2950 1735, 1645 | 0.7–1.1(6H, t-like), 1.1–1.8(44H, m), 2.28(2H, t, J=6H$_z$), 2.50(2H, d, J=6H$_z$), 3.0–3.2(1H, m), 3.5–4.4(6H, m), 4.4–4.7(1H, t-like), 5.1–5.4(1H, m), 5.77(1H, d, J=4H$_z$), 6.2–6.6(1H, d-like) |
| 25 | $C_{11}H_{23}$ | $C_{13}H_{27}CO$ | Oily | 3340, 2930 1730, 1645 | 0.7–1.1(6H, t-like), 1.1–1.8(48H, m), 2.32(2H, t, J=6H$_z$), 2.48(2H, d, J=6H$_z$), 3.3–4.3(7H, m), 4.4–4.7(1H, t-like), 4.8–5.2(1H, m), 5.75(1H, d, J=4H$_z$), 6.2–6.6(1H, d-like) |
| 26 | $C_{11}H_{23}$ | $C_{15}H_{31}CO$ | Oily | 3350, 2940 1735, 1645 | 0.6–1.1(6H, t-like), 1.1–2.0(52H, m), 2.30(2H, t, J=6H$_z$), 2.47(2H, d, J=6H$_z$), 3.5–4.3(7H, m), 4.4–4.7(1H, t-like), 4.9–5.3(1H, m), 5.75(1H, d, J=4H$_z$), 6.2–6.6(1H, d-like) |
| 27 | $C_{11}H_{23}$ | $C_{17}H_{35}CO$ | Oily | 3350, 2940 1735, 1645 | 0.6–1.1(6H, t-like), 1.1–1.9(56H, m), 2.33(2H, t, J=6H$_z$), 2.53(2H, d, J=6H$_z$), 2.9–3.2(1H, m), 3.5–4.4(6H, m), 4.5–4.8(1H, t-like), 4.9–5.4(1H, m), 5.84(1H, d, J=4H$_z$), 6.5–6.8(1H, d-like) |
| 28 | $C_{13}H_{27}$ | $C_9H_{19}CO$ | Oily | 3350, 2950 1730, 1645 | 0.7–1.0(6H, t-like), 1.0–1.8(44H, m), 2.29(2H, t, J=6H$_z$), 2.49(2H, d, J=6H$_z$), 3.5–4.3(7H, m), 4.56(1H, t, J=4H$_z$), 4.9–5.3(1H, m), 5.78(1H, d, J=4H$_z$), 6.3–6.6(1H, d-like) |
| 29 | $C_{13}H_{27}$ | $C_{11}H_{23}CO$ | Oily | 3350, 2950 1730, 1645 | 0.7–1.1(6H, t-like), 1.1–1.8(48H, m), 2.28(2H, t, J=6H$_z$), 2.50(2H, d, J=6H$_z$), 4.4–4.7(1H, t-like), 4.9–5.3(1H, m), 5.80(1H, d, J=4H$_z$), 6.4–6.6(1H, d-like) |
| 30 | $C_{13}H_{27}$ | $C_{13}C_{27}CO$ | Oily | 3350, 2950 1730, 1645 | 0.7–1.1(6H, t-like), 1.1–1.8(52H, m), 2.30(2H, t, J=6H$_z$), 2.50(2H, d, J=6H$_z$), 3.6–4.2(7H, m), 4.4–4.7(1H, t-like), 5.0–5.3(1H, m), 5.79(1H, d, J=4H$_z$), 6.4–6.7(1H, d-like) |
| 31 | $C_{13}H_{27}$ | $C_{15}H_{31}CO$ | Oily | 3350, 2950 1735, 1645 | 0.7–1.0(6H, t-like), 1.0–1.8(56H, m), 2.29(2H, t, J=6H$_z$), 2.51(2H, d, J=6H$_z$), 3.5–4.2(7H, m), 4.5–4.7(1H, t-like), 4.9–5.3(1H, m), 5.80(1H, d, J=4H$_z$), 6.4–6.6(1H, d-like) |

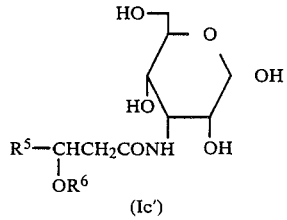

(Ic')

| 32 | $C_{11}H_{23}$ | $C_{11}H_{23}CO$ | Transparent Crystal (94-95° C.) | 3350, 2920 1720, 1635 | 0.7–1.0(6H, t-like), 1.0–1.8(38H, m), 2.1–2.9(5H, m), 3.5–5.9(12H, m) |
| 33 | $C_{11}H_{23}$ | $C_{13}H_{27}CO$ | Transparent crystal (98-99° C.) | 3350, 2920 1725, 1640 | 0.7–1.0(6H, t-like), 1.0–1.8(42H, m), 2.2–2.9(5H, m), 3.5–5.8(12H, m) |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A derivative of 3-acylamino-3-deoxyallose represented by the following formula:

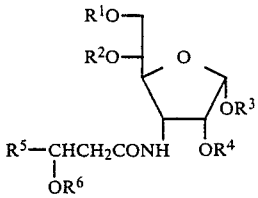

wherein $R^1$ and $R^2$ are hydrogen atoms or represent in combination an isopropylidene group, $R^3$ and $R^4$ are hydrogen atoms or represent in combination an isopropylidene group, $R^5$ represents a hydrogen atom or alkyl group, and $R^6$ represents a hydrogen atom or acyl group.

* * * * *